US008697233B2

(12) United States Patent
Kikuchi et al.

(10) Patent No.: US 8,697,233 B2
(45) Date of Patent: Apr. 15, 2014

(54) METAL-COATED LIPID BILAYER VESICLES AND PROCESS FOR PRODUCING SAME

(75) Inventors: Jun-ichi Kikuchi, Nara (JP); Yoshihiro Sasaki, Tokyo (JP); Mineo Hashizume, Tokyo (JP); Toru Imori, Ibaraki (JP)

(73) Assignees: Nara Institute of Science and Technology, Nara (JP); JX Nippon Mining & Metals Corporation, Tokyo (JP)

(*) Notice: Subject to any disclaimer, the term of this patent is extended or adjusted under 35 U.S.C. 154(b) by 1318 days.

(21) Appl. No.: 12/224,684

(22) PCT Filed: Oct. 31, 2006

(86) PCT No.: PCT/JP2006/322216
§ 371 (c)(1),
(2), (4) Date: Sep. 3, 2008

(87) PCT Pub. No.: WO2007/102253
PCT Pub. Date: Sep. 13, 2007

(65) Prior Publication Data
US 2009/0042021 A1    Feb. 12, 2009

(30) Foreign Application Priority Data

Mar. 7, 2006    (JP) ................................. 2006-061297

(51) Int. Cl.
*B32B 5/16*    (2006.01)
*B05D 3/00*    (2006.01)

(52) U.S. Cl.
USPC ........ 428/328; 428/403; 428/402.2; 428/402; 427/443.1; 427/301; 427/304; 427/299; 106/1.05

(58) Field of Classification Search
USPC ............. 106/1.05, 1.11; 428/328, 403, 443.1, 428/402–402.24, 407, 423.1, 474.4; 438/678, 687, 654; 427/301, 304, 299, 427/389.9, 213.3–213.36, 483
See application file for complete search history.

(56) References Cited

U.S. PATENT DOCUMENTS

| 5,389,496 A | 2/1995 | Calvert et al. ................ 430/315 |
| 2005/0147755 A1* | 7/2005 | Imori et al. .................... 427/299 |

FOREIGN PATENT DOCUMENTS

| EP | 0510711 | 10/1992 | .............. C23C 18/20 |
| JP | 05-202483 | * 8/1993 | .............. C23C 18/08 |

(Continued)

OTHER PUBLICATIONS

Hashizume et al., Stable vesicular nanoparticle "cerasome" as an organic-inorganic hybrid formed with organoalkoxysilane lipids having a hydrogen-bonding unit, 2003, Thin solid Films, 438-439, p. 20-26.*

Hashizume, M. et al., "Stable vesicular nanoparticle 'Cerasome' as an organic-inorganic hybrid formed with organoalkoxysilane lipids having a hydrogen-bonding unit", *Thin Solid Films*, Elsevier, 2003, vol. 438-439, pp. 20-26.

Guo, et al., "Synthesis of novel magnetic spheres by electroless nickel coating of polymer spheres", *Surface & Coatings Technology* 200 (2005) 2531-2536.

Nakagawa, et al. "Tubular and Twisted Ni-P Fibers Molded From Morphology-Tunable and Recyclable Organic Templates of Hydrogen-Bonded Supramolecular Assemblages", *Advanced Materials* 2005, 17, No. 2, Jan. 31.

*Primary Examiner* — James J Seidleck
*Assistant Examiner* — S. Camilla Pourbohloul
(74) *Attorney, Agent, or Firm* — Drinker Biddle & Reath LLP

(57) ABSTRACT

A metal-coated material comprising a metal-coated lipid bilayer vesicle and a preparation method thereof are provided. A metal-coated material comprising a metal-coated lipid bilayer vesicle having a network of siloxane bonding (Si—O—Si) on its surface. a method for preparing the metal-coated lipid bilayer vesicle comprising the following steps:

(1) rendering the functional group(s) having the ability of carrying the metal catalyst to the surface of lipid bilayer vesicle having a network of siloxane bonding (Si—O—Si bonding) on its surface, at or after the formation, by self-organization, of the lipid bilayer vesicle;
(2) immobilizing the metal catalyst on the surface of the lipid bilayer vesicle;
(3) optionally, reducing the metal catalyst; and
(4) performing electroless plating.

22 Claims, 5 Drawing Sheets

(56) References Cited

FOREIGN PATENT DOCUMENTS

| JP | 11-306855 | 5/1999 | ............... H01B 1/00 |
| JP | 3277463 | 4/2002 | ............... C23C 18/18 |
| JP | 2002-515091 | 5/2002 | ............... C23C 18/16 |
| JP | 2004-315946 | 11/2004 | ............... C23C 18/30 |
| WO | WO 96/14165 | 5/1996 | ............... B05D 7/00 |
| WO | WO 00/01862 | 1/2000 | ............... C23C 18/18 |

* cited by examiner

METAL-COATED LIPID BILAYER VESICLES AND PROCESS FOR PRODUCING SAME

TECHNICAL FIELD

This invention relates to metal-coated lipid bilayer vesicles and process for producing the same. Further, the present invention also relates to a base on which the metal-coated lipid bilayer vesicles are immobilized and process for producing it.

BACKGROUND OF THE INVENTION

"Plating" which is a technique for coating a surface of solid with metal is used for providing various functions to the surface, in addition to the traditional purpose such as providing decorative properties. For example, electrical properties (electrical conductivity, contact resistance, magnetic properties, shielding properties against electromagnetic wave, high frequency properties, etc.), mechanical properties (strength, rublicity, frictional characteristics, etc.), physical properties (solderability, bonding properties, adhesive properties, etc.), optical properties (optical reflection properties, light absorption characteristics, etc.), chemical properties (corrosion-proof properties, bactericidal properties, chemical resistance, etc.), and thermal properties (heat resistance, thermal conductivity, etc.) and the like can be provided.

Therefore, the plating technique has a wide range of the filed where the technique may be active, and it is applied in various fields such as an ornament, circuit-boards, electric contacts, semiconductor parts, lead frames, connectors, copper foils, automobile parts, electric home appliances, chemical apparatuses, plastics, engines, clocks, eyeglasses, substrates for coating, parts for electronics industry, containers, insoluble anodes, parts for printing, rubber products, sliding components, bearings, tools, rolls, building components, steel products, magnetic recording device, heat absorbing components and the like. It is predicted that the field in which the plating technique may be applied will increase.

Among the plating technique, a method for forming a metal coating without externally providing electricity is an electroless plating method. The electroless plating, which is different from an electro-plate method in which electrodeposition occurs by applying a voltage, has an advantage that a metal coating may be formed not only on metals but also on insulants such as glass, plastics and ceramics etc. Further, the electroless plating also has characteristics that it is not necessary to consider the distribution of the electric current and voltage, no anode inserted into the plating bath is required, a deposited coating is homogeneous, the thickness of the coating may become thin, plating to fine parts may be performed. Utilizing these characteristics, the electroless plating is also applied in various fields as described above.

In the field of electronics which is one of the representative filed where the electroless plating is applied, electronic parts have been significantly miniaturized and highly integrated, and their shapes have been complicated, too. Therefore, a technique for the fine plating is required (a nano-technology of top-down type). On the other hand, in the industry, a technique for assembling and constructing supermicro-mechanism at the level of atoms and molecules which has been expected to lead to an epoch-making development of materials, electronics, information communication, environment, energy, biotechnology, creation of medicament, medical service and the like is gathering much interest (a nano-technology of bottom-up type). Such a tendency of science and technology has a potential of creating a novel functional material(s) using the fine plating technique.

Under the background as described above, until now, there have been several examples where electroless plating was applied to a fine organic compound.

For example, in Hong-xia Guo et. al., "Synthesis of Novel Magnetic Spheres by Electroless Nickel Coating of Polymer Spheres", Surface & Coating Technology, Vol. 200, Elsevier B. V, 2005, p2531-2536, describes polymethylmethacrylate (PMMA) having a magnetic Ni plated layer on its surface by the electroless plating.

In this document, PMMA particles of about 1.9 μm are sensitized by adsorbing $Sn^{2+}$ on the surface of the particles using $SnCl_2$ solution, and then an oxidation-reduction reaction is caused by dipping the particles obtained into a hydrochloric acid solution of $PdCl_2$, and then metal particles of Pd are formed as a catalytic portion on the surface of PMMA particles. The obtained particles are subjected to electroless plating of Ni to form final products having an average particle diameter of 2.07 μm.

Further, in Masaru Nakagawa, "Tubular and twisted Ni—P fibers molded from morphology-tunable and recyclable organic templates of hydrogen-bonded supramolecular assemblages", Adv. Mater., Vol. 17, Wiley-VCH, 2005, p200-205, describes a hollow metal fiber wherein azopyridine carboxylic acid (APC) having propyl, methyl, sec-butyl or ethoxy group(s) is used as a template.

In this document, a fibrous molecular assemblage of APC bonded by a hydrogen bonding(s) (external diameter is about 100 nm-1 μm) is prepared. Subsequently, the fibrous molecular assemblage is soaked in an acidic aqueous solution containing $PdCl_2$ as a precursor of catalyst and then an electroless plating of Ni—P alloy is performed. Further, the obtained material is dispersed in an alkaline aqueous solution for removing the internal organic template and thus the final product is obtained.

SUMMARY OF THE INVENTION

Problem to be Solved by the Invention

While the examples of the electroless plating where an organic compound such as a polymer sphere of PMMA and super-molecular assemblage of APC is used as a template have been reported, as described in the above-mentioned documents, there have never been the case, so far as the inventors know, where an electroless plating using a lipid bilayer vesicle such as a liposome as a template was successively performed. Liposome is an artificial cell membrane which has been used mainly in the medical and pharmaceutical fields. If the liposome can be combined with the electroless plating technique, in cooperation with the wideness of the field of application of the plating technique, a quite novel functional nano-material may possibly be created.

Accordingly, one of the problems to be solved by the present invention is to provide a metal-coated lipid bilayer vesicle.

Further, another problem to be solved by the present invention is to provide a method for preparing the metal-coated lipid bilayer vesicle.

Further, yet another problem to be solved by the present invention is to provide a base on which the metal-coated lipid bilayer vesicles are immobilized.

Further, yet another problem to be solved by the present invention is to provide a process for producing the base on which the metal-coated lipid bilayer vesicles are immobilized.

Means for Solving the Problems

The inventors of the present invention eagerly studied for solving the problems, and thus, have come to take note of a substance called as cerasome. Cerasome is a lipid bilayer vesicle having a network of siloxane bonding (Si—O—Si bonding) on its surface, and thus, has a structure like a liposome coated, on its surface, with a shell. A noticeable feature of cerasome is that the size of the structure may be relatively easily defined compared to one or two dimensional systems such as fibers, lamellae and tubes. Further, it exhibits the similar behavior of phase-transition to that of liposome, and further, it shows a remarkably high stability of the structure compared to the liposome. Therefore, the inventors thought that the vesicle form may be kept under the plating condition, and further, it may be possible to plate the surface of cerasome while the hollow state (one of the features of the cerasome) is kept.

Cerasome was developed just recently, and its applications to wide range of fields from medical field to the field of material science are presently examined. With regard to cerasome, several documents have been published. For example, it is explained in details in Mineo Hashizume, Yoshihiro Sasaki, and Jun-ichi Kikuchi "Cerasome as a nano-hybrid material of three-dimensional assemblage", in The Newest Technique of Nano-Hybrid Material, CMC Publishing, 2005, p134-144; Jun-ichi Kikuchi and Kiyofumi Katagiri, "Cerasome", Dictionary of Nanotechnology, Tomoji Kawai ed., Kogyo-chosa-kai, 2003, p691-698; Mineo Hashizume and Jun-ichi Kikuchi, "Preparation of an organic-inorganic nano-hybrid cerasome having a vesicle structure and three-dimensional assemble thereof", Polymer Processing, Kobunshi-Kankokai, 2002, Vol. 51, No. 9, p413-419; Mineo Hashizume, Shin-ichi Kawanami, Shintaro Iwamoto, Takehiko Isomoto, and Jun-ichi Kikuchi, "Stable vesicular nanoparticle 'Cerasome' as an organic-inorganic hybrid formed with organoalkoxysilane lipids having a hydrogen-bonding unit", Thin Solid Films, Elsevier B.V, Vol. 438-439, 2003, p20-26. The entire disclosures of all these documents are herein incorporated by reference.

The inventors tried, at first, to perform electroless plating of Ni by providing a metal catalyst using a two liquid method (soak into $SnCl_2$ solution+soak into $PdCl_2$ solution) which is conventionally used in the field of electroless plating. However, the metal catalyst was not immobilized, and nickel was not deposited on the surface of cerasome. Therefore, we examined different conditions for performing electroless plating onto cerasome, and thus found that by providing a functional group(s) having the ability of carrying the metal catalyst onto the surface of the cerasome at or after the time of forming cerasome, the ability of carrying the metal catalyst is expressed on the cerasome and the electroless plating becomes easy.

We found that for example, when the cerasome is formed, by introducing an amphiphatic organic compound capable of forming a bilayer bearing a functional group(s) having the ability of carrying the metal catalyst, or an alkoxysilane bearing a functional group(s) having the ability of carrying the metal catalyst, the organic compound is partially incorporated into the bilayer vesicular structure of the cerasome to form a bilayer vesicle integrally with the cerasome-forming lipid, or the alkoxysilane is incorporated into the network of siloxane bonding (Si—O—Si bonding) formed on the surface of cerasome to form a bilayer vesicle integrally with the cerasome-forming lipid, and thus, the ability of carrying the metal catalyst is rendered to the surface of cerasome, and the electroless plating becomes easy (Method A). In addition, it was found that even after the formation of the cerasome, by treating the surface of the cerasome with a silane coupling agent bearing a functional group(s) having the ability of carrying the metal catalyst, the ability of carrying the metal catalyst is rendered to the surface of cerasome, and the electroless plating becomes easy (Method B).

Further, the inventors also found that cerasome immobilized on a base such as a sheet of glass can be coated with metal by rendering the ability of carrying the metal catalyst to the cerasome in the same way as described above before performing electroless plating onto the surface of the base.

The present invention has been completed on the basis of the above-described findings. Accordingly, in one aspect, the present invention is a metal-coated material comprising a lipid bilayer vesicle having a network of siloxane bonding (Si—O—Si bonding) on its surface, and a metal coating on the lipid bilayer vesicle.

Further, in another aspect, the present invention is a method for preparing the metal-coated material comprising the following steps:

(1) rendering a functional group having the ability of carrying a metal catalyst to the surface of a lipid bilayer vesicle having a network of siloxane bonding (Si—O—Si bonding) on its surface, at or after the formation, by self-organization, of the lipid bilayer vesicle;

(2) immobilizing the metal catalyst on the surface of the lipid bilayer vesicle;

(3) optionally, reducing the metal catalyst; and (4) performing electroless plating.

In one embodiment of the present invention, step (1) involves, at the formation of the lipid bilayer vesicle, introducing an amphiphatic organic compound capable of forming a bilayer by self-organization bearing a functional group having the ability of carrying a metal catalyst, or introducing an alkoxysilane bearing a functional group having the ability of carrying a metal catalyst.

In another embodiment of the present invention, step (1) involves, after the formation of the lipid bilayer vesicle, treating the surface of the lipid bilayer with a silane coupling agent bearing a functional group having the ability of carrying a metal catalyst.

Further, in another aspect, the present invention is a base on which a lipid bilayer vesicle having a network of siloxane bonding (Si—O—Si bonding) on its surface is immobilized, the lipid bilayer vesicle being coated with metal.

Further, in another aspect, the present invention is a preparation method of the base comprising the following steps:

(a) immobilizing on a base a lipid bilayer vesicle having a network of siloxane bonding (Si—O—Si bonding) on its surface by an alternating lamination using an electrostatic interaction;

(b) rendering a functional group having the ability of carrying a metal catalyst to the surface of the lipid bilayer vesicle;

(c) immobilizing the metal catalyst on the surface of the lipid bilayer vesicle; wherein the steps (a), (b) and (c) are performed in the following sequence:

(a)→(b)→(c), (b)→(c)→(a), or (b)→(a)→(c), and subsequently (d) optionally, reducing the metal catalyst;

(e) performing electroless plating.

Effects of the Invention

According to the present invention, a metal-coated lipid bilayer vesicle and a preparation method thereof and a base on which a metal-coated lipid bilayer vesicle is immobilized and a preparation method thereof are provided.

DESCRIPTION OF THE PREFERRED EMBODIMENT

Cerasome

Figure 1:
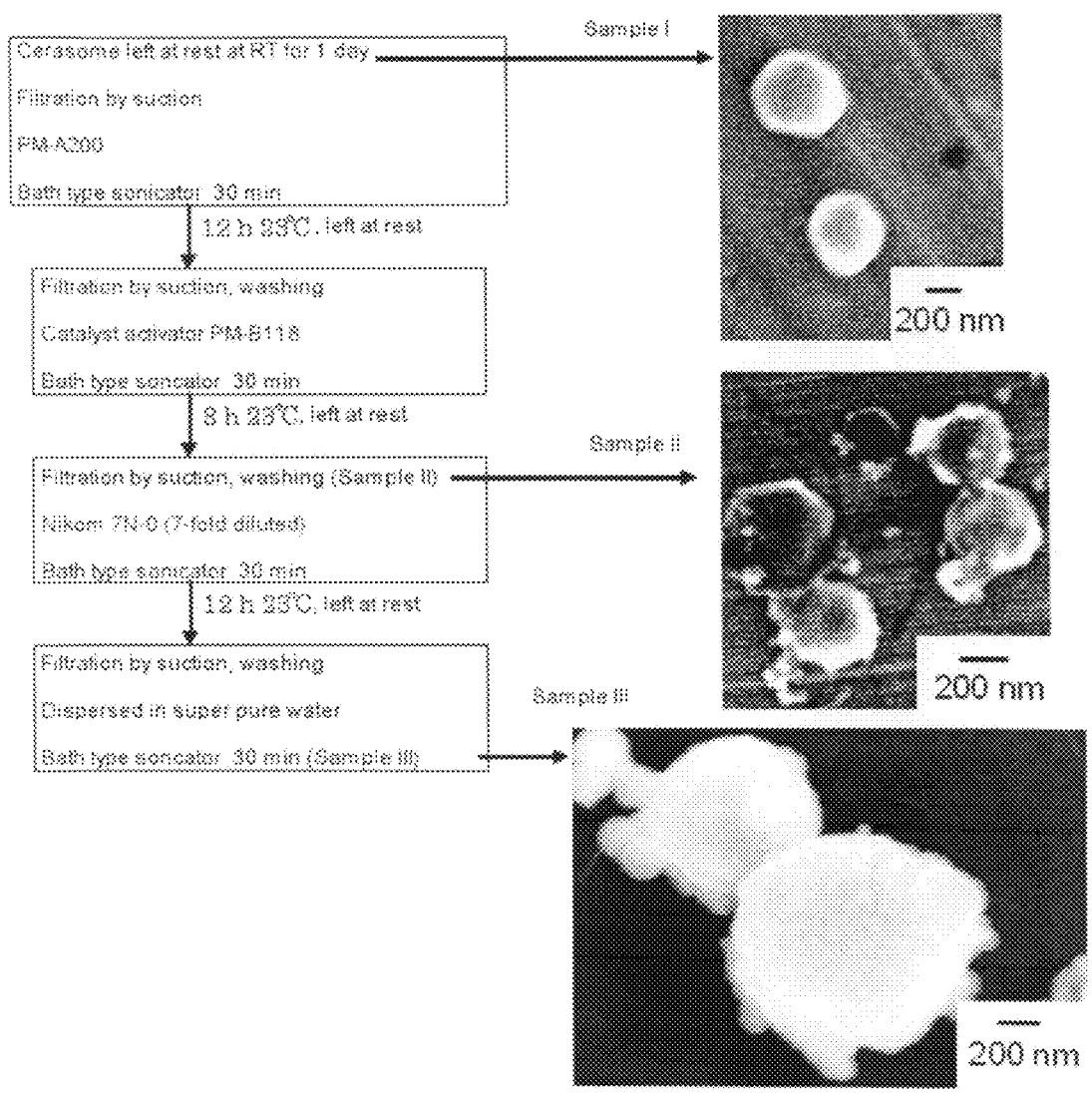
FIG. 1 shows the preparation procedure of Ni-coated cerasome, and SEM images of each process (Example 1).

In the present specification, "cerasome" indicates a lipid bilayer vesicle having a network of siloxane bonding (Si—O—Si bonding) on its surface, they being used interchangeably. A cerasome suitable for using in the present invention may be prepared by using, as a material, a lipid molecule which self-organizes a bilayer vesicle in water and, has the structure capable of forming a network of siloxane bonding on the surface of the bilayer vesicle by hydrolysis and polycondensation reaction (sol-gel reaction) (hereafter, referred to as "cerasome-forming lipid"). The cerasome may be made of a single layer, or also may be made of multilayers of nested boxes structure where a small cerasome is incorporated in a large cerasome.

As an example of a cerasome-forming lipid, lipid molecules which have both of alkoxysilyl group and hydrophobic group are mentioned. When a site where hydrogen bonding zone is formed additionally exists between alkoxysilyl group and hydrophobic group, the stability of morphology may preferably increase. When this lipid molecule is dispersed in water, the lipid becomes amphoteric as a result of hydrolysis of alkoxysilyl group, a bilayer vesicular structure inside of which is hollow is spontaneously formed. Subsequently, a cerasome is formed by development of a network of siloxane derived from polycondensation of alkoxysilyl groups of neighbor lipids. Cerasome-forming lipid(s) for forming a cerasome may be identical or different. The morphological stability of cerasome is controlled by the critical charging parameters in the same way as the conventional liposome. In this regard, see J. N. Israelachvili, D. J. Mitchell, B. W. Ninham, J. Chem. Soc., Faraday Trans., Vol. 2, No. 72, 1976, p1525-1568 (The content of the document is incorporated into the present specification).

As alkoxysilyl groups, for example, ones having at least one, preferably three of a $C_1$-$C_{20}$, preferably $C_1$-$C_{10}$, and more preferably $C_1$-$C_6$ linear, branched or circular alkoxy group(s) are mentioned, more preferably the three alkoxy groups being identical. As alkoxy group, for example, methoxy, ethoxy, propoxy, isopropoxy, butoxy, isobutoxy, sec-butoxy, tert-butoxy, pentyloxy, hexyloxy, cyclopropyloxy, cyclopentyloxy, cyclohexyloxy and the like are mentioned. As it is necessary to set up an appropriate condition for hydrolysis of lipid for forming the cerasome, ones having methoxy, ethoxy or propoxy group are preferable. Further, in some cases where the hydrolysis of lipid and formation of the membrane structure proceed simultaneously according to the preparation condition of cerasome, trimethoxysilyl, triethoxysilyl or tripropoxysilyl group is more preferable as the alkoxysilyl group because they make it possible to form a stable membrane structure even under such preparation conditions.

As a hydrophobic group, substituted or unsubstituted hydrocarbon groups, which may be identical each other or not, having 10 or more carbon atoms are preferable, and substituted or unsubstituted linear alkyl groups, which may be identical each other or not, having 10 or more carbon atoms are more preferable, and linear alkyl groups having 12-20 carbon atoms are still more preferable, due to the reason for stabilizing the bilayer structure of cerasome. As the substituent, ether, carbonyl, ester, thioether, thiocarbonyl, thioester, amino, amide, imide, azo, urethane, and urea groups are mentioned. From the viewpoint of stabilization of the membrane structure by intermolecular interaction, amide group and urea group are preferable. Further, these hydrophobic groups are preferably two strands which have been bonded to the same atom (e.g., a nitrogen atom or carbon atom), and they are more preferably identical.

As a site for hydrogen bonding, any group which binds the alkoxysilyl group and the hydrophobic group, and allows the formation of hydrogen bonding zone in membrane may be passable. However, a divalent group(s) including an amide bond(s), urethane bond(s) or urea bond(s) having both of hydrogen donor site and hydrogen acceptor site is(are) more preferable because it is intended to stabilize the hydrogen bonding zone in the membrane.

Examples of cerasome-forming lipids are indicated concretely below (lipid 1-6):

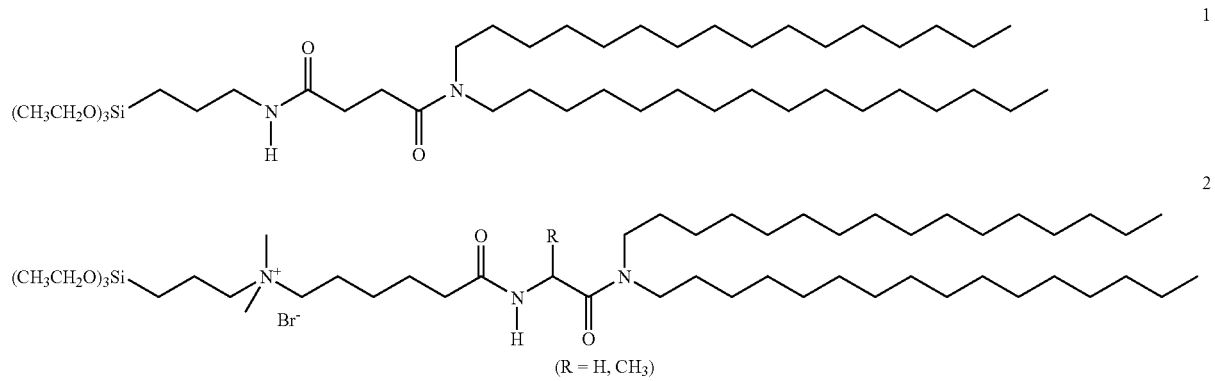

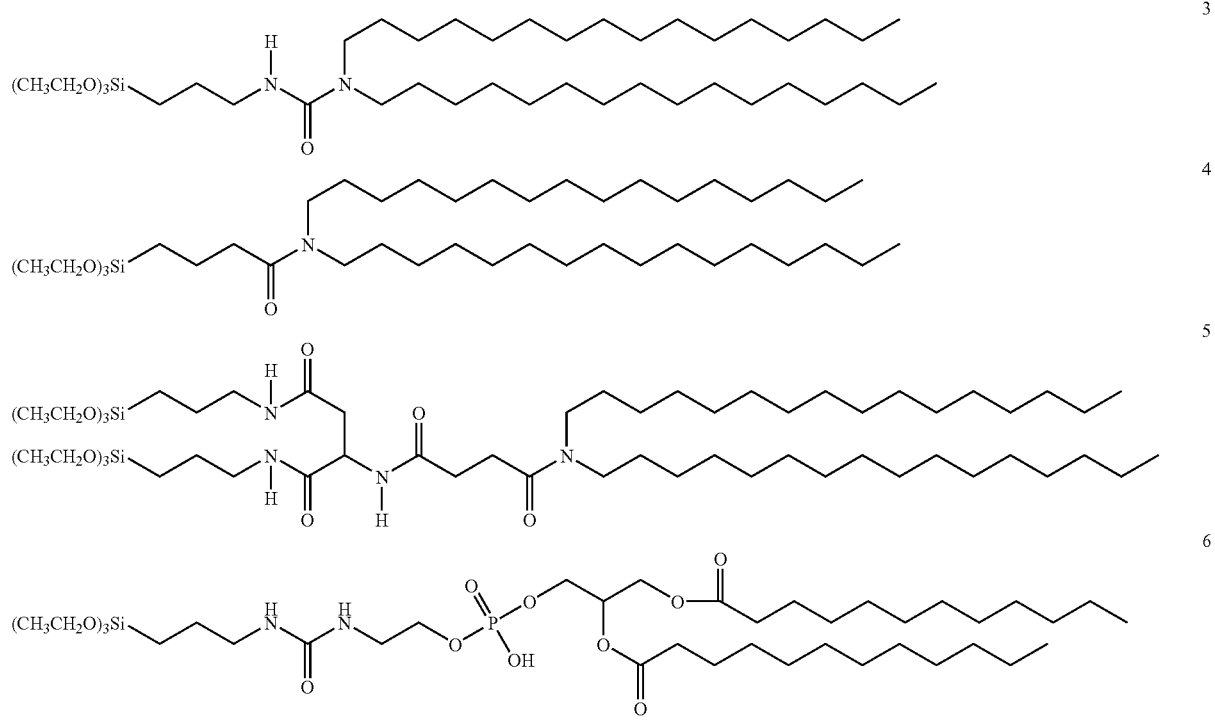

Cerasome may be prepared, for example, by a method wherein the above-described cerasome-forming lipid(s) is(are) directly dispersed in water, and an alcohol injection method wherein the cerasome-forming lipid is injected into water after the alkoxy group(s) is(are) hydrolyzed in alcohol such as ethanol. However, the methods for preparing cerasome are not limited to these methods.

While a direct dispersion method is a simple method for preparing a cerasome, it is necessary to strictly adjust the pH of water for some lipids used. For example, when a cerasome is prepared using a cerasome-forming lipid 1 which is not an amphiphatic compound, it is important to adjust the pH closely to 3. This is for proceeding the hydrolysis of alkoxy group, subsequent spontaneous formation of molecular assemblage, and the polycondensation between silanol groups, in a well-balanced manner. Under the condition of pH 1 where the acid hydrolysis and polycondensation are accelerated, a cerasome cannot prepared from the lipid 1, and a precipitate occurs. On the other hand, when a cerasome is prepared using a compound such as lipid 2 which has been amphiphatic originally, a cerasome may be formed under any pH condition.

In preparation of cerasome by an alcohol injection method, a lipid is first dissolved in alcohol and then alkoxy group(s) is(are) hydrolyzed by addition of a very small amount of water and acid. Subsequently, a dispersion solution of cerasome can be prepared by pouring this alcohol solution into water. This alcohol injection method can be applied to almost cerasome-forming lipids, and has an advantage that it can be applied to the compound(s) having a low dispersion property to water.

The particle diameter of cerasome can be controlled by a dispersion method in the same way as the conventional vesicles. Namely, the particle diameter of cerasome can be controlled by controlling the degree of the mechanical agitation at the formation of the vesicles. While a mechanical agitation by a Vortex mixer is usually performed for enhancing the dispersion property, a sonication is more effective. While usually the agitation is performed for a time sufficient for obtaining the desired particle diameter, usually about 0.5-15 hours are required for obtaining the particle diameter of about 100-700 nm. Further, it is also possible to make the particle diameter small by decreasing the parameter of critical packing of lipid. While the sonication is particularly effective for decreasing the particle diameter of cerasome, it is dependent on the molecular structure of lipid.

The cumulant average particle diameter of cerasome thus obtained may be controlled within the range of about 30 nm-10 μm. For example, in the case of lipid 2, while a multilayer cerasome of about 200 nm of diameter is obtained when only the mechanical agitation by Vortex mixer is used, it can be converted into a cerasome having a mono layer vesicle structure of diameter of about 30-50 nm by performing a subsequent sonication. In the present specification, "cumulant average particle diameter" indicates the average particle diameter calculated by analyzing the data obtained by a dynamic light scattering method by using Cumulant method.

Cerasome exhibits a remarkable high morphological stability several hours after the cerasome was prepared (namely, the agitation was completed), because the polycondensation between the silanol groups proceeds on the surface of the membrane with time while the siloxane network on the surface is not sufficiently developed in water immediately after the preparation of cerasome. Therefore, when the surface treatment or plating treatment to the cerasome is performed several hours (e.g., 3 hours or more, preferably, more than 24 hours) after the cerasome was prepared, collapse of the vesicle structure of the cerasome during the treatment may be prevented. However, a partial development of the siloxane network on the surface of the cerasome is sufficient for preventing the collapse, a complete development of the network being not required. Usually, the polymerization degree of oligomer is able to provide a sufficient morphological stability.

Further, it is also possible to add the several functions by chemically modifying the surface of cerasome. For example, in the case where the cerasome is prepared by an alcohol injection method, when an appropriate cross-linking agent such as tetraethoxysilane (TEOS) is coexisted, a cerasome in which the siloxane network has more developed is obtained, and it is also possible to further reinforce the morphological stability. Further, when 3-aminopropyltriethoxysilane is coexisted at the preparation of the cerasome, the surface of the cerasome obtained may be modified with amino group(s). Through this amino group(s), it is also possible to introduce several functional groups and to immobilize the biomolecule(s). Further, when metal alkoxide such as tetraalkoxy titanium is coexisted at the preparation of the cerasome, in the same way as described above, the functional cerasome the surface of which is modified with the metal alkoxide may be prepared. In the present invention, the metal-coated cerasome having a modified surface is also aimed.

As described above, cerasome has an increased mechanical strength due to the formation of the siloxane network on its surface. Therefore, it is known that the cerasome can be immobilized on the base by an alternating lamination using the electrostatic interaction while the vesicle structure is kept. At this process, the alternating lamination of cationic cerasome and anionic cerasome can be performed, or a layer of an anionic or cationic polymeric electrolyte can be partially incorporated.

For example, a cerasome formed of lipid 1 behaves in water as a polyanionic colloidal nano-capsule under neutral condition, and therefore, an alternating lamination of this cerasome and poly(diallyldimethylammonium chloride) (PDDA) which is a cationic polymer can be performed. The alternating lamination can be performed easily by dipping a base alternately into a dispersing aqueous solution of cerasome and an aqueous solution of polymer.

Immobilization of Metal Catalyst

While cerasome can be metal-coated by an electroless plating using an ordinary means, it is preferable, from the viewpoint of bonding property, adhesion property and evenness of the metal for plating, to previously immobilize a metal catalyst on the cerasome by providing a functional group(s) having an ability of carrying a metal catalyst onto the surface of cerasome. An appropriate embodiment thereof is given below.

As a functional group(s) having the ability of carrying a metal catalyst, any hydrophilic groups capable of carrying a metal catalyst usually used in the electroless plating (e.g., precious metals such as palladium, silver, platinum, gold, rhodium, iridium and the like) may be used without any particular limitation. As such functional groups, several functional groups capable of forming a salt or complex against a metal ion(s) may be mentioned, carboxyl, sulfonic, mercapto, phosphoric, phosphonic, dithiocarbamic, amino, imino, azole, ether, ketone groups and the like being concretely mentioned. Among them, azole groups are preferable, and as azole groups, imidazole, oxazole, thiazole, selenazole, pyrazole, isooxazole, isothiazole, triazole, oxadiazole, thiadiazole, tetrazole, oxatriazole, thiatriazole, bendazole, indazole, benzimidazole, bezotriazole groups and the like are mentioned, imidazole group being particularly preferable.

In the first method, when the cerasome is prepared, an amphiphatic organic compound capable of forming the bilayer bearing a functional group(s) having the ability of carrying a metal catalyst, or alkoxysilane bearing a functional group(s) having the ability of carrying a metal catalyst is introduced and integrated with the cerasome-forming lipid, and thus a lipid bilayer vesicle is formed. By the process, onto the surface of the cerasome, a functional group(s) having the ability of carrying a metal catalyst is(are) rendered, and thus the electroless plating becomes easy (Method A).

The amphiphatic organic compound may have the similar hydrophobic group(s) and optional hydrogen bonding zone site as described above with regard to the cerasome. It is preferable, from the viewpoint of forming a bilayer vesicle structure integrated with the cerasome-forming lipid, to have the same hydrophobic group(s) and hydrogen bonding zone site as the cerasome-forming lipid used. Further, the alkoxysilane may have the similar alkoxy group(s) as described above with regard to the cerasome, methoxy, ethoxy or propoxy group being preferable for forming a stable membrane structure. The number of alkoxy groups included in one molecule of the alkoxysilane is 1-3, it being preferably 3 from the viewpoint of forming a stable membrane structure. As examples of such alkoxysilane, 3-aminopropyl trimethoxysilane, 3-aminopropyl triethoxysilane, N-2 (aminoethyl) 3-aminopropyl methyldimethoxysilane, N-2 (aminoethyl) 3-aminopropyl methyldiethoxysilane are mentioned.

The mixing proportion of the amphiphatic organic compound or the alkoxysilane and cerasome-forming lipid is not particularly limited. However, when the proportion of the cerasome-forming lipid is too much small, the morphological stability of bilayer vesicle obtained becomes insufficient. On the other hand, when the proportion is too much large, a sufficient ability of carrying a metal catalyst can not be rendered to the cerasome. Therefore, the proportion in molar ratio is preferably about 50:50-1:999, more preferably about 50:50-1:99.

To the cerasome, to which a functional group(s) having the ability of carrying a metal catalyst has(have) been thus rendered onto its surface, a metal catalyst can be immobilized by a conventional means known to those skilled in the art. For example, a metal catalyst may be immobilized on the cerasome, by contacting (e.g., by dipping, spray, application) the cerasome with a solution containing chloride, hydroxide, oxide, sulfate, amine complex such as ammonium salt of precious metals such as palladium, silver, platinum, gold, rhodium, iridium and the like, especially with a solution containing palladium chloride (e.g., aqueous solution or a water-containing organic solution).

In the second method, the surface of cerasome is treated with a silane coupling agent bearing a functional group(s) having the ability of carrying a metal catalyst after the formation of the cerasome. By this treatment, a functional group(s) having the ability of carrying a metal catalyst is(are) rendered onto the surface of the cerasome, and thus the electroless plating becomes easy (Method B).

The silane coupling agent may be obtained by reacting:
an organic compound(s) bearing a functional group(s) having the ability of carrying a metal catalyst, as described above, preferably, azole compound(s), more preferably, imidazole compound(s); and
a silane coupling agent(s) having at least one hydrolyzable group bound to silicon atom (for example, halogen group such as chloro group, alkoxy group, acetoxy group, isopropenoxy group, amino group) and at least one organic functional group (for example, epoxy, glycidyl, vinyl, styryl, acryloxy, methacryloxy, amino, N-phenylaminopropyl, ureido, chloropropyl, mercapto, isocyanate, sulfide group).

As the hydrolyzable group, alkoxy groups are preferable from the viewpoint of affinity to the surface of cerasome, stability and tractability. As alkoxy groups, for example, linear, branched or circular alkoxy groups of $C_{1-20}$, preferably $C_{1-10}$, more preferably $C_{1-6}$ may be mentioned, more concretely, e.g., methoxy, ethoxy, propoxy, isopropoxy, butoxy, isobutoxy, sec-butoxy, tert-butoxy, pentyloxy, hexyloxy, cyclopropyloxy, cyclopentyloxy, cyclohexyloxy groups and the like being mentioned.

As a silane coupling agent bearing a functional group(s) having the ability of carrying a metal catalyst which may be preferably used in the present invention, a silane coupling agent obtained by reaction of azole compounds and epoxysilane compounds as described in Japanese Patent Application Public Disclosure No. 6-256358 may be exemplified, the entire of the content being incorporated into this specification.

As epoxysilane compounds, the epoxysilane coupling agent (e.g., γ-glycidoxypropyltrimethoxysilane) indicated by the following general formula is particularly preferable:

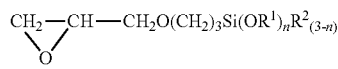

wherein $R^1$ and $R^2$, which may be identical or different, are alkyl group of $C_{1-3}$, and n is 1-3.

As azole compounds, benzoimidazole and imidazole are particularly preferable. The reaction of azole compounds and epoxysilane compounds can be performed under the condition indicated in Japanese Patent Application Public Disclosure No. 6-256358. For example, at 80-200° C., to one molar azole compound, 0.1-10 moles of epoxysilane compound is added dropwise and they are reacted for 5 minutes-2 hours. For this process, any solvent is not particularly required. However, an organic solvent such as chloroform, dioxane, methanol, ethanol and the like may be used.

The surface treatment for rendering a functional group(s) having the ability of carrying a metal catalyst to the surface of the cerasome can be performed by contacting (e.g., by dipping, spray, application) the cerasome with a solution of silane coupling agent having the functional group(s) having the ability of carrying a metal catalyst (as a solution, a water-soluble solvent such as water, alcohol, and mixture thereof may be used).

Subsequently, immobilization of the metal catalyst onto the cerasome can be performed by contacting it (e.g., by dipping, spray, application) with a solution containing chloride, hydroxide, oxide, sulfate, amine complex such as ammonium salt of precious metals such as palladium, silver, platinum, gold, rhodium, iridium and the like, which becomes a metal catalyst, especially with a solution containing palladium chloride (such as an aqueous solution or water-containing organic solution). However, it is preferable that the metal catalyst containing organic solution is previously mixed or reacted with the silane coupling agent to prepare a solution in which the silane coupling agent carries the metal catalyst, and then the surface treatment is performed with the solution, because the bonding property of the plating increases.

The concentration of the silane coupling agent having the functional groups having the ability of carrying the metal catalyst in the silane coupling agent solution is not limited. However, 0.001-10% by weight is preferable. When the concentration is less than 0.01% by weight, the amount of the silane coupling agent bonded to the surface of the cerasome decreases and therefore it is difficult to accomplish the effect. On the other hand, when the concentration is greater than 10% by weight, the amount bonded to the cerasome becomes too much, and therefore it is difficult to dry the cerasome, and the cerasome often aggregates.

Metal Coating

The cerasome onto which a metal catalyst has been immobilized can be metal-coated by an electroless plating using the conventional means known to those skilled in the art. For example, the metal-coated cerasome can be obtained by dispersing the cerasome in a plating solution, for the electroless plating, containing the ions of desired metals (e.g., nickel, cobalt, iron, tin, palladium, copper, silver, gold, platinum, lead, rhodium, ruthenium, and the like), and performing the electroless plating. It is usually treated with the solution containing a reducing agent corresponding to the metal for plating (e.g., $H_3PO_2$ (hypophosphorous acid), $NaH_2PO_2$ (sodium hypophosphite), dimethylamine borane (DMAB), $NaBH_4$, $KBH_4$, $NH_2NH_2$, HCHO, $SnCl_2$, $CH_4NH_2S$, and the like), for increasing the catalytic activity, and then dispersed in the plating solution. The reducing treatment can be performed, for example, by contacting the cerasome, onto which the metal catalyst has been immobilized, with the reducing solution (e.g., by dipping, spray, or application). In addition, into the plating solution, any conventional additives known to those skilled in the art such as complexing agent, stabilizing agent, surfactant and pH adjustor may be added.

In one embodiment of the metal-coated material according to the present invention, it is possible to make the inside of the material hollow. In order to accomplish this, the above-described process for preparing the metal-coated cerasome:

(1) rendering the functional group(s) having the ability of carrying the metal catalyst to the surface of lipid bilayer vesicle having a network of siloxane bonding (Si—O—Si bonding) on its surface, at or after the formation, by self-organization, of the lipid bilayer vesicle;

(2) immobilizing the metal catalyst on the surface of the lipid bilayer vesicle;

(3) optionally, reducing the metal catalyst; and (4) performing electroless plating should be performed under the temperature environment where the lipid bilayer vesicle keeps its gel state, because the vesicle based on the cerasome exhibits the behavior of phase-transition, namely, over the phase-transition temperature, the morphological stability thereof decreasing because of phase-transition to liquid crystal state where the hydrophobic group(s) is(are) molten. On the other hand, when the temperature is too low, the formation of the vesicle becomes difficult, and therefore, the low temperature is not preferable. Accordingly, in the process, the temperature of organic solvents, aqueous solutions, water-containing organic solution and a plating bath used and the like is usually controlled to about 10-90° C., preferably about 20-70° C.

Conversely, when it is intended to penetrate the metal into the inside of the material, the process may be performed at the temperature raised to the level at which the bilayer vesicle structure of cerasome is not collapsed.

After the electroless plating, the metal-coated cerasome may be obtained in the form dispersed in water by adding the metal-coated material of cerasome into water and agitating, and also obtained in the form of powder (the inside of which is typically hollow) by drying the dispersed one. The thickness of the metal-coating in the metal-coated material may be about 1 nm-about 1 μm. The cumulant average particle diameter of the metal-coated material may be controlled to the range from about 30 nm to about 10 μm. The controls may be performed by means, e.g., setting up the reaction conditions (time, temperature, concentration) for the plating treatment.

While the physical properties of the metal-coated materials related to the present invention are now studied, they are relatively flexible because of being able to be hollowed, unlike the simple metallic powder, and characteristically have a low density. Further, the cerasome can be relatively easily controlled in its particle diameter, and therefore, the metal-coated materials related to the present invention using the cerasome are also relatively easily controlled in their particle diameter. By controlling the surface charge of the cerasome, a high dimensional orientation may be possible. Further, when magnetic property is rendered to the cerasome which has entrapped internally various materials, by the electroless plating of iron, nickel, cobalt and the like onto the surface of the cerasome, the transfer of the materials may be controlled by the magnetic properties.

Metal Coating of the Cerasome on the Base

As described above, the cerasome can be laminated and immobilized on the base by an alternating lamination using the electrostatic interaction while the vesicle structure is kept. It is possible, by the electroless plating, using an ordinary means, to perform the metal-coating of the cerasome immobilized on the base. However, from the viewpoint of bonding property, adhesion property and evenness of the metal for plating, a method of performing the electroless plating to the cerasome having the functional group(s) having the ability of carrying a metal catalyst in the surface thereof is preferable.

Accordingly, in one of the embodiments of the present invention, the cerasome on the base is metal-coated by performing the following steps:

(a) immobilizing a lipid bilayer vesicle having a network of siloxane bonding (Si—O—Si bonding) on its surface on a base, by an alternating lamination using an electrostatic interaction;

(b) rendering a functional group(s) having the ability of carrying the metal catalyst to the surface of the lipid bilayer vesicle;

(c) immobilizing the metal catalyst on the surface of the lipid bilayer vesicle; wherein the steps (a), (b) and (c) are performed in the following sequence:

(a)→(b)→(c), (b)→(c)→(a), or (b)→(a)→(c), and subsequently (d) optionally, reducing the metal catalyst;

(e) performing electroless plating.

In any case where steps (a), (b) and (c) are performed in one of the sequences as indicated above, the step (b) can be performed, by treating the surface of the lipid bilayer vesicle formed, with the silane coupling agent having the functional group(s) having the ability of carrying the metal catalyst, after the formation of the lipid bilayer vesicle.

In the case where the steps (a), (b) and (c) are performed in the sequence (b)→(c)→(a), or (b)→(a)→(c), namely, in the embodiment where the functional group(s) having the ability of carrying the metal catalyst is(are) rendered to the surface of the cerasome, and then the cerasome is immobilized onto the base, the step (b) can be performed by introducing, at the formation of the lipid bilayer vesicle, an amphiphatic organic compound having the functional group(s) having the ability of carrying the metal catalyst and able to form a bilayer membrane by self-organization for forming the lipid bilayer vesicle.

When the cerasome is immobilized on the base after the functional group(s) having the ability of carrying the metal catalyst is(are) rendered to the surface of the cerasome, the immobilization of the functional group(s) onto the surface of the base itself may be prevented, and the base may be selectively metal-coated at the place where the cerasome is immobilized. Conversely, when the surface treatment is performed after the immobilization of cerasome to the base, a portion(s) where the cerasome has not been immobilized on the base is(are) also rendered the ability of carrying the metal catalyst, and therefore, it may be difficult to selectively metal-coat the cerasome.

Further, when the base which has originally the ability of carrying the metal catalyst is used, the metal catalyst may be immobilized on the surface of the base merely by contacting the base with the solution containing the metal catalyst (e.g., an aqueous solution or a water-containing organic solution). In such a case, the cerasome is immobilized on the base after the step where the metal catalyst is immobilized on the cerasome. Namely, the process is performed in the sequence (b)→(c)→(a), for preventing the contact of the base itself to the metal catalyst, and thus, the immobilization of the metal catalyst onto the portion other than the portion where the cerasome has been immobilized on the base may be avoided.

The step (c) may be performed, for example, by contacting the solution containing chloride, hydroxide, oxide, sulfate and/or amine complex of one, two or more of precious metal(s) selected from the group consisting of palladium, silver, platinum, gold, rhodium and iridium (e.g., an aqueous solution or a water-containing organic solution) with the lipid bilayer vesicle.

As a metal catalyst, a functional group(s) having the ability of carrying the metal catalyst, a silane coupling agent having the functional group(s) having the ability of carrying the metal catalyst, and an amphiphatic organic compound having the functional group(s) having the ability of carrying the metal catalyst and capable of forming a bilayer membrane by self-organization, ones previously exemplified may be used.

The cerasome immobilized on the base, the metal catalyst having been additionally immobilized onto the cerasome, may be metal-coated by an electroless plating using the conventional means known to those skilled in the art. For example, a metal-coated cerasome immobilized on the base may be obtained by contacting (e.g., by dipping, spray, application) the electroless plating solution containing the ions of the desired metal(s) (e.g., nickel, cobalt, iron, tin, palladium, copper, silver, gold, platinum, lead, rhodium, ruthenium, and the like) with the cerasome immobilized on the base and performing the electroless plating. It is usually treated with the solution (e.g., an aqueous solution or water-containing organic solution) containing a reducing agent corresponding to the metal for plating (e.g., $H_3PO_2$ (hypophosphorous acid), $NaH_2PO_2$ (sodium hypophosphite), dimethylamine borane (DMAB), $NaBH_4$, $KBH_4$, $NH_2NH_2$, HCHO, $SnCl_2$, $CH_4NH_2S$, and the like), for increasing the catalytic activity, and then contacted with the plating solution. The reducing treatment can be performed, for example, by contacting the cerasome immobilized on the base with the reducing solution (e.g., by dipping, spray, or application). In addition, into the plating solution, any conventional additives known to those skilled in the art such as complexing agent, stabilizing agent, surfactant and pH adjustor may be added.

The surface of the base which may be used in the present invention is not particularly limited provided that it is comprised of the material onto which the cerasome may be laminated and immobilized by the alternating lamination using the electrostatic interaction, namely the material capable of being anionically or cationically ionized (e.g., metals such as copper, nickel and tantalum, glass, ceramics, mica, quartz, epoxy-resin, polyimide-resin, PET and liquid crystal polymer). Further, in the embodiment where the cerasome on the base is selectively metal-coated, a base having no catalytic activity, namely a base wherein a metal may not be deposited on its surface by an ordinary means of an electroless plating for example, dipping into the solution containing the metal catalyst+dipping into the solution containing the reducing agent+dipping into the electroless plating solution) is preferable from the viewpoint of the selective plating, e.g., glass, mica, quartz, epoxy-resin, polyimide-resin, PET and liquid crystal being mentioned as such a base.

It is preferable, for facilitating the immobilization of cerasome onto the base, to wash the base and perform the anionic or cationic ionization of the surface of the base, before the immobilization. For example, organic substance(s) and the like are sonicated in alcohol (e.g., in 2-propanol), and then the surface of the base is dipped into a water—an ammonia water—an aqueous solution of hydrogen peroxide for anionic ionization.

As described above, in several embodiments of the present invention, the metal-coating of the base may be selectively performed to the portion where the cerasome has been immobilized. The cerasome is selectively laminated to the portion cationically or anionically ionized on the base. Therefore, a fine metallic wiring pattern(s) may be made by patterning the portions to be cationically or anionically ionized on the base. Accordingly, in several embodiments of the present invention, an electrical circuit(s) may be made by the metal(s) on the base.

EXAMPLES

Several working examples are provided below so that the present invention will be more exactly understood by reference to them, which are not ones to limit the present invention.

Example 1

Preparation of the Powder of Ni-Coated Cerasome (Method B)

(1) Synthesis of the Cerasome-Forming Lipid

N,N-dihexadecyl-N'-[(3-triethoxysilyl)propyl]urea: $(EtO)_3 SiC_3U2C_{16}$ (lipid3), which is one of the cerasome-forming lipids, was synthesized according to the following process.

Dihexadecylamine (0.523 g, 1.15 mmol) was dissolved in dichloromethane (30 mL), and 3-triethoxysilyl isocyanate (0.331 g, 1.34 mmol) was added and agitated for 1 hour. The solvent was removed by distillation, and a column chromatography [Wako-gel C-300; hexane-ethyl acetate (5:1 v/v)] was performed, and thus a colorless transparent oily substance was obtained. Yielded amount (Yield): 0.523 g (73.3%). TLC: Rf value 0.19 (Silica gel $60F_{254}$ MERCK, hexane-ethyl acetate (5:1 v/v)). $^1$H-NMR (600 MHz, $CDCl_3$, TMS): δ0.63 [2H, t, J=7.6 Hz, $SiCH_2$], 0.87 [6H, t, J=6.8 Hz, $CH_3$], 1.20-1.25 [61H, m, $(CH_2)_{13}CH_3$, $OCH_2CH_3$], 1.5-1.63 [4H, m, $NCH_3CH_2$, $SiCH_2CH_2$], 3.13 [4H, t, J=7.4 Hz, $NCH_2$], 3.22 [2H, t, J=6.8 Hz, $CH_2NHCO$], 3.81 [6H, q, J=6.9 Hz, $OCH_2CH_3$], 4.43 [1H, br, NHCON]. Element analysis: Measured value: C, 70.47%; H, 12.73%; N, 3.69%. Calculated value as $C_{42}H_{88}N_2O_4Si$: C, 70.73%; H, 12.44%; N, 3.93%.

(2) Preparation of Cerasome 12.9 mg of cerasome-forming lipid compound $(EtO)_3 SiC_3U2C_{16}$ (lipid 3), preparation liquid 217 μL were added into a micro tube so that $(EtO)_3SiC_3U2C_{16}$ (lipid 3): HCl: $H_2O$:ethanol=1:0.03:19:200 (molar ratio), and then the mechanical agitation was performed using a Vortex mixer for 12 hours. 120 μL of sol solution obtained was added dropwise into 20 ml of ultrapure water at 35° C. with stirring, and thus 0.5 mM cerasome aqueous dispersion was obtained. The cumulant average particle diameter was 200 nm (Ohtsuka Denshi K.K., Type: DLS-6000).

(3) Preparation of Ni-Coated Cerasome

FIG. 1 shows the outline of the procedure. 5 mL of aqueous dispersion of cerasome left at rest for 24 hours after it was prepared (Sample I) was filtrated with a membrane filter with a pore diameter of 25 nm by sucking, and then added into an electroless plating pre-treatment agent (Nikko Materials, PM-A200) which is an aqueous solution of imidazole type silane coupling agent containing 20 mg/L $Pd^{2+}$, and was dispersed by sonication for 30 minutes. The sample was left at rest at 23° C. for 12 hours, filtrated by sucking and then washed. Thus prepared cerasome carrying $Pd^{2+}$ was added to a catalyst activator (Nikko Materials, PM-B118, an aqueous solution containing a reducing agent as an main component), and then dispersed by sonication for 30 minutes using a bath-type sonicator. After leaving the sample at rest for 8 hours, filtration by sucking and washing were performed (Sample II). Subsequently, the cerasome thus pre-treated was added to a medium content phosphorus type electroless nickel plating solution (Nikko Metal Plating, Nikom 7N-0),

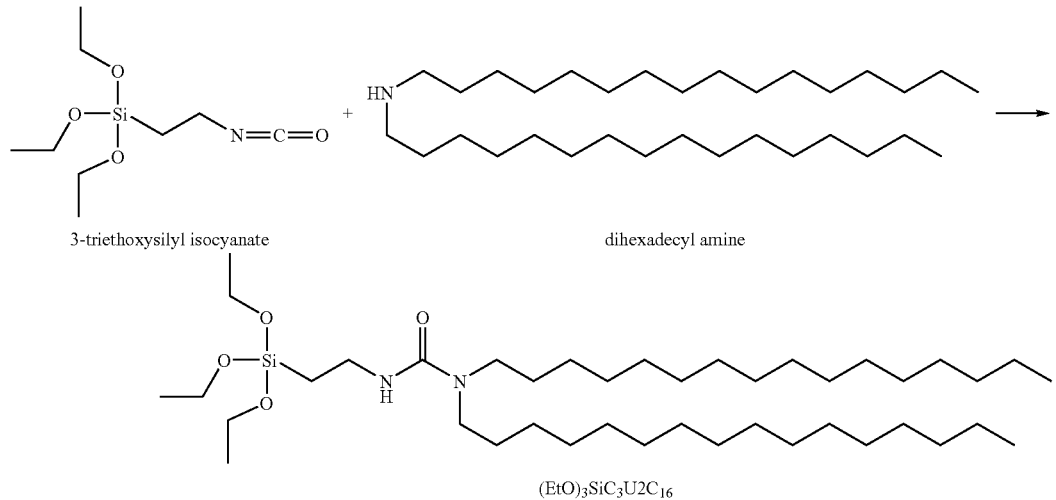

3-triethoxysilyl isocyanate dihexadecyl amine $(EtO)_3SiC_3U2C_{16}$ and then dispersed by sonication for 30 minutes, and left at rest for 12 hours, and thus a black product was obtained. The black product obtained was added into 5 mL of ultrapure water, ant then dispersed by sonication for 30 minutes. The suspension was cast onto an aluminum foil, and dried at room temperature in the air for one day (Sample III). Free-flowing black powder was obtained.

(4) Result

The results of FE-SEM observation (Nihon Denshi K.K., Type JSM-6301F) for Samples I, II and III were shown in FIG. 1. Further, as a result of EDS measurement (Nihon Denshi K.K., Type JED-2201), existence of Pd on the surface of Sample II was confirmed (existence of particles of Pd may also be confirmed by SEM image), and it was confirmed that the whole surface of Sample III was evenly coated with Ni. P content in Ni was about 8% from the result of the quantitative determination by EDS. The cumulant average particle diameter was 400 nm.

Figure 3:
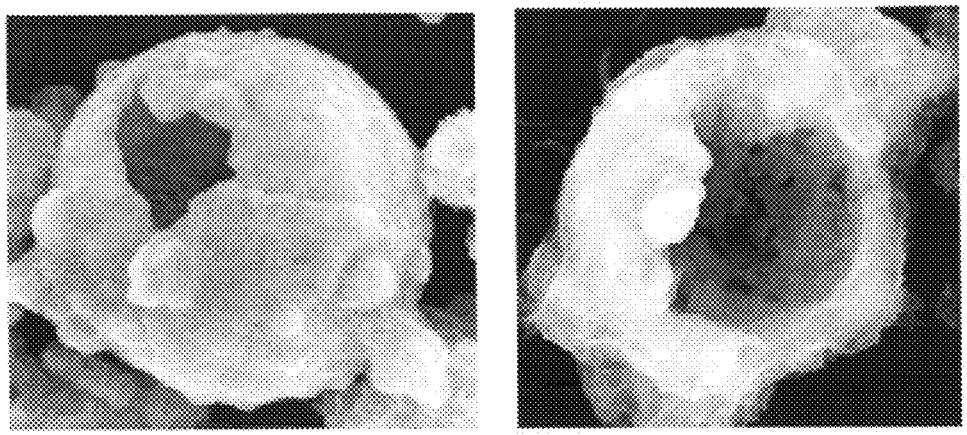
FIG. 3 is SEM images showing that the inside of the metal coated cerasome is hollow (Example 1).

Further, when the metal-coated cerasome obtained was calcined for removing the internal aqueous phase and organic compound, and then observed by FE-SEM, a metallic capsule the surface of which had been partially lacked was confirmed, as shown in FIG. 3. It was confirmed, from this observation, that the inside of the Ni-coated cerasome was hollow.

Example 2

Preparation of the Powder of Ni-Coated Cerasome (Method A)

(1) Synthesis of an Imidazole Ligand Having a Hydrophobic Long Chain

NHCH$_2$CH$_2$CH$_2$], 6.79 [1H, s, NCHC], 7.52 [1H, d, J=1.1 Hz, NCHNH]. Element analysis: Measured value: C, 69.46%; H, 11.20%; N, 14.97%. Calculated value as C$_{42}$H$_{88}$O$_4$N$_4$Si: C, 69.79%; H, 11.18%; N, 14.80%.

(2) Preparation of Ligand-Mixed Cerasome

Preparation of Ligand-Mixed Cerasome was Performed, as Described Below, Using the cerasome-forming lipid compound of Example 1 (EtO)$_3$SiC$_3$U2C$_{16}$ (lipid 3) and an imidazole ligand His UC$_{16}$ having a hydrophobic long chain synthesized above.

9.6 mg of cerasome-forming lipid compound (EtO)$_3$SiC$_3$U2C$_{16}$, 149.5 μL of 10 mM ethanol solution of imidazole ligand His UC$_{16}$ were added into a micro tube so that (EtO)$_3$SiC$_3$U2C$_{16}$, His UC$_{16}$=9:1 (molar ratio). To this, 30.0 μL of a preparation solution (HCl: H$_2$O: ethanol=0.03:19:1.6 (molar ratio)) was added so that ((EtO)$_3$SiC$_3$U2C$_{16}$+His UC$_{16}$):HCl: H$_2$O:EtOH=1:0.03:19:200 (molar ratio), and then the mechanical agitation was performed using a Vortex mixer for 12 hours. 120 μL of a sol solution obtained was added dropwise to 20 mL of ultrapure water at 35° C. with stirring, and thus 0.5 mM ligand-mixed cerasome aqueous dispersion was obtained. The cumulant average particle diameter was 200 nm.

(3) Preparation of Ni-Coated Cerasome

Figure 2:
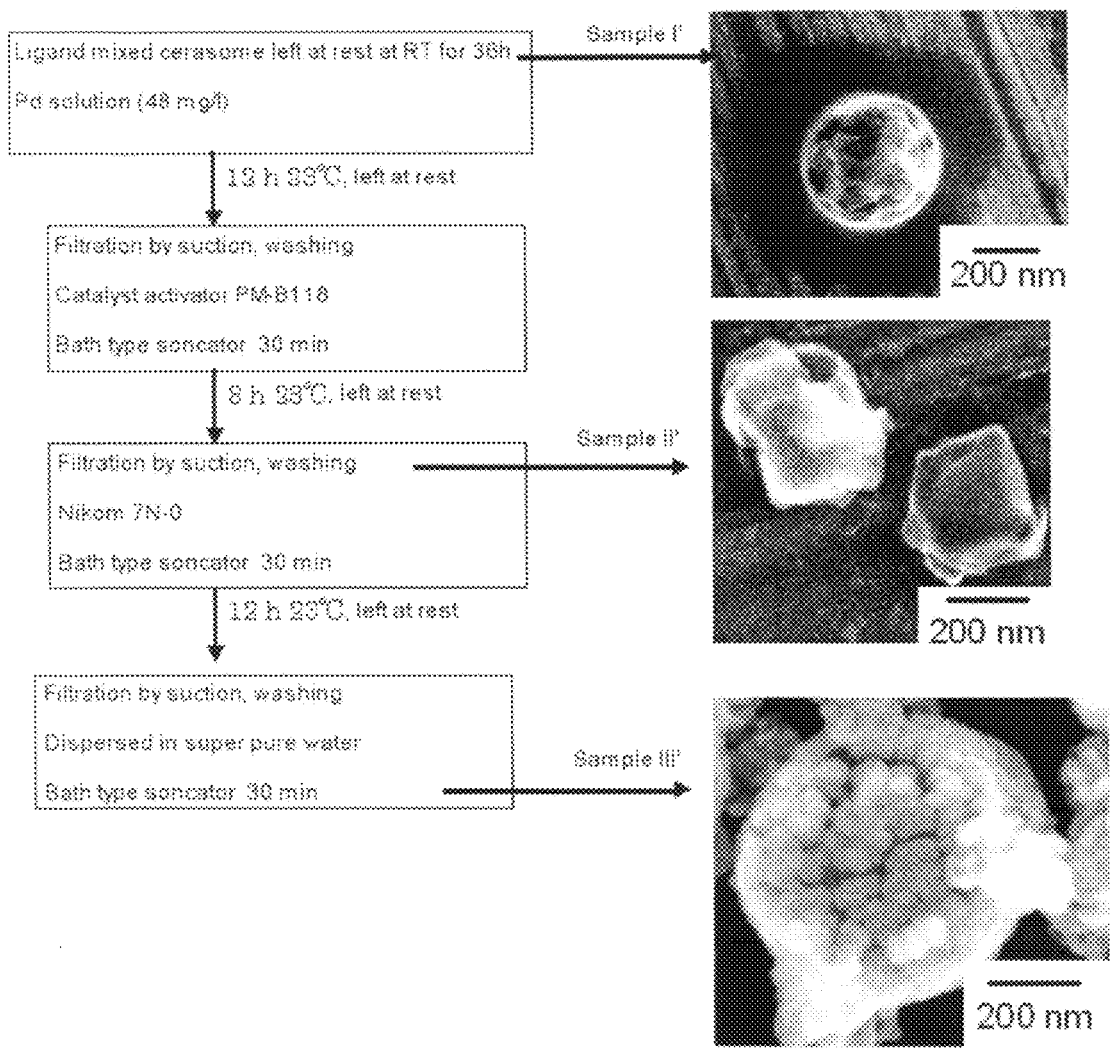
FIG. 2 shows the preparation procedure of Ni-coated ligand-mixed cerasome, and SEM images of each process (Example 2).

FIG. 2 shows the outline of the procedure. To 5mL of aqueous dispersion of ligand-mixed cerasome left at rest for 36 hours after it was prepared (Sample I'), 40.2 μL of Pd$^{2+}$ solution was added (Pd$^{2+}$ concentration 48 mg/L). The sample was left at rest at 23° C. for 12 hours, filtrated with a membrane filter with a pore diameter of 25 nm by sucking and washed. Thus prepared cerasome carrying Pd$^{2+}$ was added to

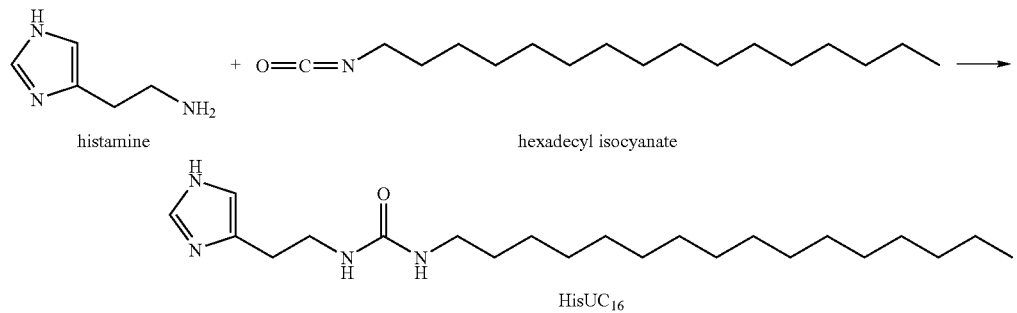

An imidazole ligand His UC$_{16}$ having a hydrophobic long chain was synthesized as an amphiphatic organic compound for effectively accomplishing the coordination of Pd$^{2+}$ on the surface of cerasome, from histamine and hexadecyl isocyanate, according to the following process.

Histamine (0.351 g, 3.2 mmol) was dissolved in 20 mL of distilled chloroform, and 4 mL of distilled triethylamine and hexadecyl isocyanate (0.825 g, 3.1 mmol) were added, and stirred at 60° C. for 50 hours. After removing the solvent by distillation, a white solid obtained was purified by a column chromatography (Wako-gel C-300; chloroform-methanol (4:1 v/v)). A white solid (melting point 129.5° C.) was obtained. Yielded amount (Yield): 1.03 g (87.8%). TCL: Rf value 0.60 (Silica-gel 60F$_{254}$MERCK, chloroform-methanol (4:1 v/v)). $^1$H-NMR (600 MHz, CDCl$_3$:CDCl$_3$ (4:1 v/v), TMS): δ0.88 [3H, t, J=7.1 Hz, CH$_3$], 1.23-1.31 [26H, m, (CH$_2$)$_{13}$CH$_3$], 1.45 [2H, qn, J=7.0 Hz, NHCH$_2$CH$_2$CH$_2$], 2.75 [2H, t, J=6.9 Hz, NHCH$_2$CH$_2$CH$^2$], 3.10 [2H, t, J=7.1 Hz, NHCH$_2$CH$_2$CH$_2$C], 3.35 [2H, t, J=7.1 Hz, a catalyst activator (Nikko Materials, PM-B118), and then dispersed by sonication for 30 minutes using a bath-type sonicator. After leaving the sample at rest for 8 hours, filtration by sucking and washing were performed (Sample II'). Subsequently, the cerasome thus pre-treated was added to an electroless nickel plating solution (Nikko Metal Plating, Nikom 7N-0), and then dispersed by sonication for 30 minutes, and left at rest for 12 hours, and thus a black product was obtained. The black product obtained was added into 5 mL of ultrapure water, and then dispersed by sonication for 30 minutes. The suspension was cast onto an aluminum foil, and dried at room temperature in the air for one day (Sample III'). Free-flowing black powder was obtained.

(4) Result

The results of FE-SEM observation for Samples I', II' and III' were shown in FIG. 2. Further, as a result of EDS measurement, existence of Pd on the surface of Sample II' was confirmed, and it was confirmed that the whole surface of Sample III' was coated with Ni. P content in Ni—P alloy was about 8% from the result of the quantitative determination by EDS (Nihon Denshi K.K., Type JED-2201). The cumulant average particle diameter was 400 nm. It was confirmed, on the basis of the comparison of the samples III and III', that III is superior in the evenness of metal-coating.

Comparative Example 1

After the preparation of cerasome (without mixing ligand) according to the operation in Example 1, the operation of the electroless plating was performed in the same way as in Example 1, except that a palladium chloride solution ($Pd^{2+}$ concentration 50 mg/L) was used instead of an electroless plating pre-treatment agent (Nikko Materials, PM-A200). Nickel was hardly deposited on the surface of the cerasome.

Example 3

Ni-Coating of Cerasome Immobilized on the Base (1) Washing of a Quartz Base

A quartz base (9×30×1 mm) was soaked in 2-propanol, and washed at room temperature by sonication (a bath type sonicator) for 1 hour, washed with ethanol, and then dried by spraying nitrogen gas. Subsequently, the quartz base was soaked in a washing solution ($H_2O$:25% ammonia water:29% aqueous solution of hydrogen peroxide=5:1:1 v/v/v) at 70° C., for one hour and thus an anionic property was rendered to the surface of the quartz base.

(2) Deposition and Immobilization of Ligand-Mixed Cerasome and Cerasome onto a Glass Base The treated quartz base was soaked in 10 mL of aqueous dispersion of ligand-mixed cerasome prepared in Example 2 (in a plastic container) and left at rest at 50° C. for 1 hour. The cerasome behaves as a cationic vesicular particle under the condition since its isoelectric point is about 4, and therefore, the ligand-mixed cerasome was accumulated and immobilized by an alternating lamination using an electrostatic interaction with the anionized quartz base. 1,2-dimyristoyl-sn-glycero-3-phosphoethanolamine-N-(Lissaminerhodamine B sulfonyl) (ammonium salt) (hereafter, Rho-PE) was incorporated into the ligand-mixed cerasome to confirm the immobilization of cerasome by measuring the fluorescence spectrum. It was confirmed, from the increase of the fluorescence strength at 590 nm where Rho-PE exhibits the fluorescence, that the ligand-mixed cerasome was immobilized on the base.

(3) Electroless Plating

To three type of the base, i.e., the base to which the ligand-mixed cerasome had been immobilized, the base to which the cerasome containing no ligand had been immobilized, for a comparison experiment, and the base merely washed, electroless plating was performed. Into the $Pd^{2+}$ solution at 60° C. ($Pd^{2+}$ concentration 24 mg/l), these bases were soaked for 10, 30 and 60 minutes, respectively. After rinsing with water, they were soaked in the catalyst activator (Nikko Materials, PM-B118), at 60° C. for 5 minutes. After rinsing with water, they were soaked in the electroless nickel plating solution (Nikko Metal Plating, Nikom 7N-0) for 2 minutes and then rinsed with water.

(4) Result

As for the quartz base to which the ligand-mixed cerasome had been immobilized, it was confirmed that the base was significantly plated with Ni by soaking it in $Pd^{2+}$ solution for only 10 minutes. However, with regard to the quartz base to which the cerasome containing no ligand had been immobilized, it was confirmed that only the base soaked in $Pd^{2+}$ solution for 60 minutes was significantly plated. As for the quartz base merely washed, it was confirmed that Ni was hardly deposited, even when it was soaked in $Pd^{2+}$ solution for 60 minutes.

Example 4

Preparation of the Powder of Magnetic Metal-coated Cerasome (Method A)

(1) Preparation of Ligand-Mixed Cerasome

Ligand-mixed cerasome was prepared in the same way as in Example 2. 15.2 mg of cerasome-forming lipid compound $(EtO)_3SiC_3U2C_{16}$, 21.5 μL of 10mM ethanol solution of imidazole ligand His $UC_{16}$ were added into a micro tube so that $(EtO)_3SiC_3U2C_{16}$, His $UC_{16}$=99:1 (molar ratio). To this, 237 μL of a preparation solution ($HCl:H_2O$:ethanol=0.03:19:182.9 (molar ratio)) was added so that $((EtO)_3SiC_3U2C_{16}$+His $UC_{16}$): $HCl:H_2O$:EtOH=1:0.03:19:200 (molar ratio), and then the mechanical agitation was performed using a Vortex mixer for 12 hours. 121.0 μL of a sol solution obtained was added dropwise to 20 mL of ultrapure water, at 35° C., with stirring, and thus 0.5 mM ligand-mixed cerasome dispersion aqueous solution was obtained. The cumulant average particle diameter was 250 nm.

(2) Preparation of Magnetic Metal Coated Cerasome

To 10 mL of aqueous dispersion of ligand-mixed cerasome left at rest for at least 24 hours after it was prepared (Sample I"), 40 μL of $Pd^{2+}$ solution was added ($Pd^{2+}$ concentration 24 mg/L). The sample was left at rest at 25° C. for 12 hours, filtrated with a membrane filter having a pore diameter of 50 nm by sucking and washed. Thus prepared cerasome carrying $Pd^{2+}$ was added to a catalyst activator (Nikko Materials, PM-B118), and then dispersed by sonication for 5 minutes using a bath-type sonicator. After leaving the sample at rest at 25° C. for 8 hours, filtration by sucking and washing were performed (Sample II"). Subsequently, the cerasome thus pre-treated was added to 7.5 mL of electroless magnetic metal plating solution, 2.5 mL of 1 mol/L NaOH aqueous solution was added and then dispersed by sonication for 5 minutes, and left at rest at 25° C. for 30-120 minutes, and thus a black product was obtained. The black product obtained was added into 2.5 mL of ultrapure water, and then dispersed by sonication for 5 minutes. The suspension was cast onto an aluminum foil, and dried at room temperature in the air for one day (Sample III"). Free-flowing black powder was obtained.

The electroless magnetic metal plating solution was prepared by making reference to that described in Japanese Patent Application Public Disclosure No. 2002-270426. Namely, it is comprised of 0.1 mol/L dimethylamine borane, 0.061 mol/L cobalt sulfate heptahydrate, 0.004 mol/L nickel sulfate (II) hexahydrate, 0.035 mol/L iron sulfate (II) heptahydrate, 0.2 mol/L ammonium sulfate, 0.02 mol/L sodium citrate, 0.35 mol/L sodium tartrate, 0.06 mol/L phosphorous acid (phosphonic acid). From the plating solution having such composition, a magnetic metal coating containing Co, Ni, Fe, and B, where Co content is 40-80 at %, Fe content is 15-40 at %, Ni content is 5-20 at %, and B content is 0.5-5 at % is obtained.

(3) Result

Figure 4:
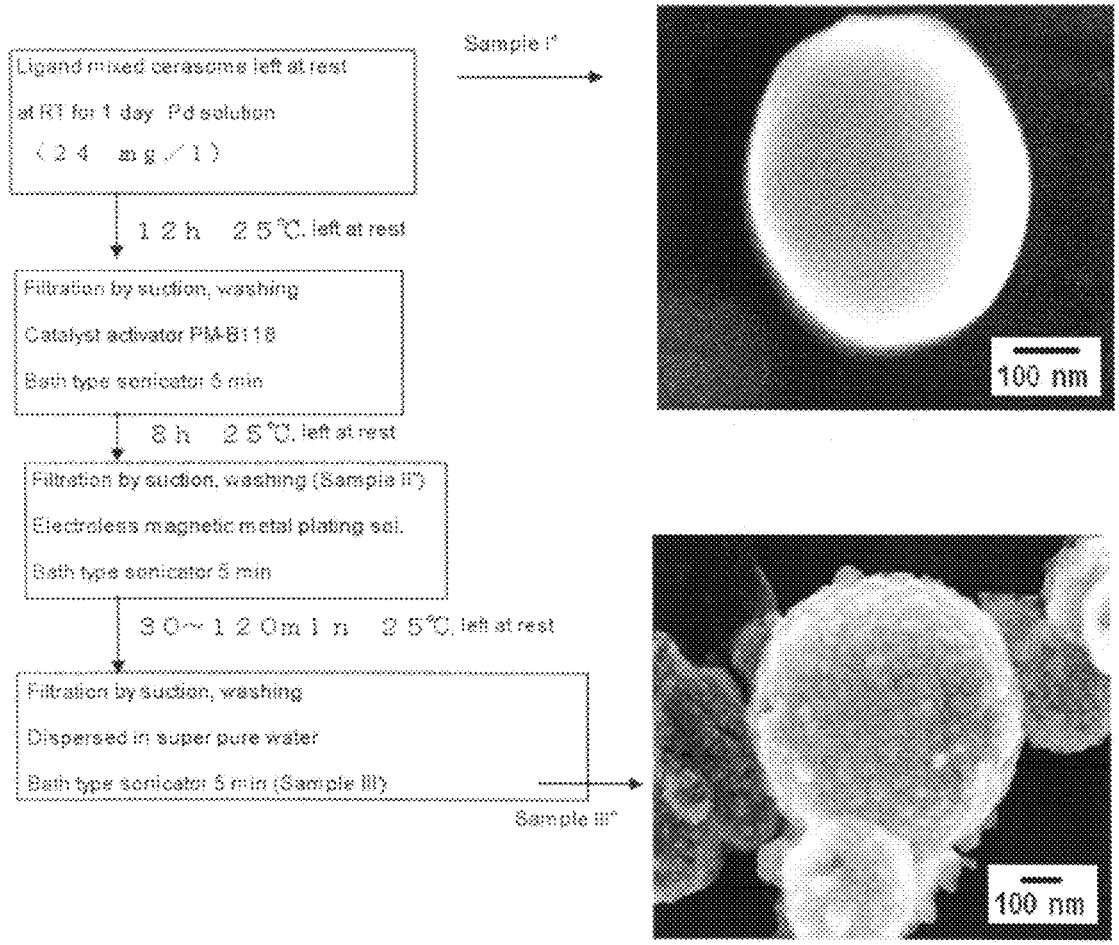
FIG. 4 shows the preparation procedure of a magnetic metal-coated ligand-mixed cerasome, and SEM images of each process (Example 4).

The results of FE-SEM observation for Samples I", III" were shown in FIG. 4. Further, as a result of EDS measurement, the whole surface of Sample III" was coated with magnetic metal. The metal composition of the magnetic metal material, which was quantitatively determined by EDS, was Co 58%, Fe 35%, Ni 7%.

Figure 5:
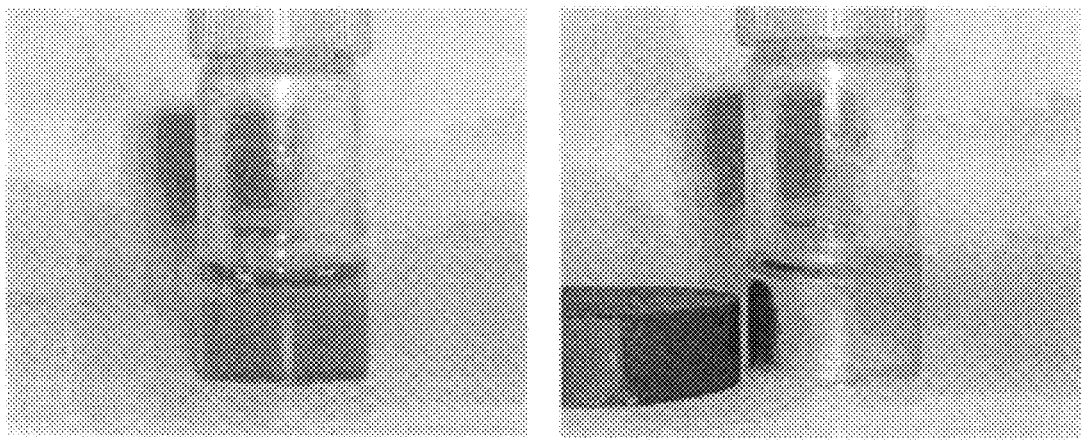
FIG. 5 is a photograph showing the state where the magnetic metal-coated cerasome is drawn toward magnet (Example 5).

Further, when a magnet was placed near the suspension, the magnetic metal-coated cerasomes in the suspension were drawn near the magnet within several seconds and aggregated, and the solution became transparent. This behavior was shown in FIG. 5.

AVAILABILITY IN INDUSTRIES

Metal-coated lipid bilayer vesicle according to the present invention may be in the form of a hollow powder of diameter of about 30 nm-about 10 μm. Therefore, when various materials are entrapped in the powder, and then the magnetic property is rendered to it by performing the electroless plating of iron, nickel, cobalt and the like to the surface of the powder, the transfer of the materials may be controlled by the magnetic properties. In addition, when the coating metal is appropriately selected, it may be used as a fine functional material for modifying the electrical properties (electrical conductivity, contact resistance, magnetic properties, shielding properties against electromagnetic wave, high frequency properties, etc.), mechanical properties (strength, rublicity, frictional characteristics, etc.), physical properties (solderability, bonding properties, adhesive properties, etc.), optical properties (optical reflection properties, light absorption characteristics, etc.), chemical properties (corrosionproof properties, bactericidal properties, chemical resistance, etc.), and thermal properties (heat resistance, thermal conductivity, etc.) and the like.

Further, according to the present invention, a base can be selectively metal-coated, and therefore, it is deemed to be useful as a method for "assembling the required amount of the material(s) having the desired properties to the portion requiring it(them)". Further, the present invention also makes it possible to form a fine metallic wiring pattern(s). In addition, the application as a micro-particulate capsule where catalytically active site may be effectively used will be possible by rendering the catalytic activity to the surface metal of the metal-coated cerasome, while the conventional catalysts of metallic particles have reactive sites merely at the surface and thus the internal metallic portion cannot be used.

In addition, the present invention may be applied in the various fields such as an ornament, circuit-boards, electric contacts, semiconductor parts, lead frames, connectors, copper foils, automobile parts, electric home appliances, chemical apparatuses, plastics, engines, clocks, eyeglasses, substrates for coating, parts for electronics industry, containers, insoluble anodes, parts for printing, rubber products, sliding components, bearings, tools, rolls, building components, steel products, magnetic recording device, heat absorbing components and the like.

The invention claimed is:

1. A hollow metal-coated material comprising:
   a lipid bilayer vesicle having a network of siloxane bonding (Si—O—Si bonding) on its surface, wherein a functional group having the ability of carrying a metal catalyst is rendered to the surface of the lipid bilayer vesicle, said functional group being selected from the group consisting of carboxyl, sulfonic, mercapto, phosphoric, phosphonic, dithiocarbamic, amino, imino, azole, ether, and ketone groups, and combinations thereof, whereby the metal catalyst is immobilized on the surface of the lipid bilayer vesicle, and
   a metal coating on the lipid bilayer vesicle having said siloxane bonding network.
2. The metal-coated material according to claim 1, wherein the metal catalyst contains one or more metals selected from the group consisting of palladium, silver, platinum, gold, rhodium and iridium, 3. The metal-coated material according to claim 1, wherein the metal coating contains one or more metals selected from the group consisting of nickel, cobalt, iron, tin, palladium, copper, silver, gold, platinum, lead, rhodium and ruthenium.

4. The metal-coated material according to claim 1, in the form of powder.

5. The metal-coated material according to claim 1, wherein it is provided in the form of a water dispersion.

6. The metal-coated material according to claim 4 or 5, having a cumulant average particle diameter from 30 nm to 10 μm.

7. A preparation method for preparing the metal-coated material according to claim 1, comprising the following steps:
   (1) rendering a functional group having the ability of carrying a metal catalyst to the surface of a lipid bilayer vesicle having a network of siloxane bonding (Si—O—Si bonding) on its surface, at or after the formation, by self-organization, of the lipid bilayer vesicle, said functional group being selected from the group consisting of carboxyl, sulfonic, mercapto, phosphoric, phosphonic, dithiocarbamic, amino, imino, azole, ether, and ketone groups, and combinations thereof;
   (2) immobilizing a metal catalyst on the surface of the lipid bilayer vesicle;
   (3) optionally, reducing the metal catalyst; and
   (4) performing electroless plating;
wherein steps (1) to (4) are performed under a temperature environment where the lipid bilayer vesicle maintains a gel state.

8. The preparation method according to claim 7, wherein step (2) comprises contacting the lipid bilayer vesicle with an aqueous solution containing chloride, hydroxide, oxide, sulfate and/or ammmne complex of one or more precious metals selected from the group consisting of palladium, silver, platinum, gold, rhodium and iridium.

9. The preparation method according to claim 7, wherein step (3) is performed and comprises contacting the lipid bilayer vesicle on the surface of which the metal catalyst has been immobilized with $H_3PO_2$ (hypophosphorous acid), $NaH_2PO_2$ (sodium hypophosphite), dimethylamine borane (DMAB), $NaBH_4$, $KBH_4$, $NH_2NH_2$, HCHO, $SnCl_2$, $CH_4NH_2S$, or a mixture thereof.

10. The preparation method according to claim 7, wherein step (1) includes, at the formation of the lipid bilayer vesicle, introducing an amphiphatic organic compound capable of forming a bilayer by self-organization bearing the functional group having the ability of carrying a metal catalyst, or introducing an alkoxysilane bearing the functional group having the ability of carrying metal catalyst.

11. The preparation method according to claim 7, wherein step (1) includes, after the formation of the lipid bilayer vesicle, treating the surface of the lipid bilayer vesicle with a silane coupling agent bearing the functional group having the ability of carrying a metal catalyst.

12. An article comprising a base on which a hollow lipid bilayer vesicle having a network of siloxane bonding (Si—O—Si bonding) on its surface is immobilized, wherein a functional group having the ability of carrying a metal catalyst is rendered to the surface of the lipid bilayer vesicle, said functional group being selected from the group consisting of carboxyl, sulfonic, mercapto, phosphoric, phosphonic, dithiocarbamic, amino, imino, azole, ether, and ketone groups, and combinations thereof,
whereby the metal catalyst is immobilized on the surface of the lipid bilayer vesicle, and the lipid bilayer vesicle having said siloxane bonding network is coated with metal.

13. The article according to claim 12, wherein the metal catalyst contains one or more metals selected from the group consisting of palladium, silver, platinum, gold, rhodium and iridium.

14. The article according to claim 12, wherein the coating metal contains one or more metals selected from the group consisting of nickel, cobalt, iron, tin, palladium, copper, silver, gold. platinum, lead, rhodium and ruthenium.

15. The article according to claim 12, wherein the surface material of the base on which the lipid bilayer vesicle is immobilized is selected from the group consisting of glass, mica, quartz, epoxy-resin, polyimide-resin, PET and liquid crystal polymer.

16. The article according to claim 12, wherein the base is selectively metal-coated at the place where the lipid bilayer vesicle is immobilized.

17. The article according to claim 16, wherein the metal on the base forms a circuit.

18. A preparation method for preparing the article according to claim 12, comprising the following steps:
   (a) immobilizing on a base a lipid bilayer vesicle having a network of siloxane bonding (Si—O—Si bonding) on its surface by an alternating lamination using an electrostatic interaction;
   (b) rendering a functional group having the ability of carrying a metal catalyst to the surface of the lipid bilayer vesicle, said functional group being selected from the group consisting of carboxyl, sulfonic, mercapto, phosphoric, phosphonic, dithiocarbamic, amino, imino, azole, ether, and ketone groups, and combinations thereof;
   (c) immobilizing the metal catalyst on the surface of the lipid bilayer vesicle; wherein the steps (a), (b) and (c) are performed in the following sequence;
   (a)→(b)→(c), (b)→(c)→(a), or (b)→(a)→(c), and subsequently
   (d) optionally, reducing the metal catalyst; and
   (e) performing electroless plating;
   wherein steps (1) to (4) are performed under a temperature environment where the lipid bilayer vesicle maintains a gel state.

19. The preparation method according to claim 18, wherein the steps (a), (b) and (c) are performed in the sequence (b)→(c)→(a), or (b)→(a)→(c), and the step (b) comprises, at the formation of the lipid bilayer vesicle, introducing an amphiphatic organic compound capable of forming a bilayer by self-organization bearing the functional group having the ability of carrying a metal catalyst, or introducing an alkoxysilane bearing the functional group having the ability of carrying a metal catalyst.

20. The preparation method according to claim 18, wherein the step (c) comprises contacting the lipid bilayer vesicle with an aqueous solution containing chloride, hydroxide, oxide, sulfate and/or ammine complex of one or more precious metals selected from the group consisting of palladium, silver, platinum, gold, rhodium and iridium.

21. The preparation method according to claim 18, wherein the step (d) is performed and comprises contacting the lipid bilayer vesicle on the surface of which the metal catalyst has been immobilized, with $H_3PO_2$ (hypophosphorous acid), $NaH_2PO_2$ (sodium hypophosphite), dimethylamine borane (DMAB), $NaBH_4$, $KBH_4$, $NH_2NH_2$, HCHO, $SnCl_2$, $CH_4NH_2S$, or a mixture thereof.

22. The preparation method according to claim 18, wherein the step (b) comprises, after the formation of the lipid bilayer vesicle, treating the surface of the lipid bilayer vesicle with a silane coupling agent hearing the functional group having the ability of carrying a metal catalyst.

* * * * *

UNITED STATES PATENT AND TRADEMARK OFFICE
CERTIFICATE OF CORRECTION

PATENT NO. : 8,697,233 B2
APPLICATION NO. : 12/224684
DATED : April 15, 2014
INVENTOR(S) : Jun-ichi Kikuchi et al.

Page 1 of 1

It is certified that error appears in the above-identified patent and that said Letters Patent is hereby corrected as shown below:

In the Claims:

Column 21, line 67, the "," at the end of the line should be a ".".

Column 22, line 34, "ammmne" should read --amine--.

Column 23, line 8, "gold." should read --gold,--.

Column 24, line 33, "hearing" should read --bearing--.

Signed and Sealed this
Fifth Day of August, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,697,233 B2  
APPLICATION NO. : 12/224684  
DATED : April 15, 2014  
INVENTOR(S) : Jun-ichi Kikuchi et al.

Page 1 of 1

It is certified that error appears in the above-identified patent and that said Letters Patent is hereby corrected as shown below:

In the Claims:

Column 21, line 67, the "," at the end of the line should be a ".".

Column 22, line 34, "ammmne" should read --ammine--.

Column 23, line 8, "gold." should read --gold,--.

Column 24, line 33, "hearing" should read --bearing--.

This certificate supersedes the Certificate of Correction issued August 5, 2014.

Signed and Sealed this  
Seventh Day of October, 2014

Michelle K. Lee  
*Deputy Director of the United States Patent and Trademark Office*